(12) United States Patent
Toole

(10) Patent No.: US 6,754,523 B2
(45) Date of Patent: Jun. 22, 2004

(54) METHOD OF ANALYSIS OF THE ELECTROCARDIOGRAM

(76) Inventor: J. Gerald Toole, 151 East Laurel, Suite 104, Lake Forest, IL (US) 60045

(*) Notice: Subject to any disclaimer, the term of this patent is extended or adjusted under 35 U.S.C. 154(b) by 395 days.

(21) Appl. No.: 09/996,273

(22) Filed: Nov. 28, 2001

(65) Prior Publication Data

US 2002/0082510 A1 Jun. 27, 2002

Related U.S. Application Data

(60) Provisional application No. 60/253,575, filed on Nov. 28, 2000.

(51) Int. Cl.$^7$ .............................. A61B 5/04
(52) U.S. Cl. ...................... 600/509; 600/512
(58) Field of Search ................... 600/508, 509, 600/512, 516, 517

(56) References Cited

U.S. PATENT DOCUMENTS

| | | | |
|---|---|---|---|
| 4,697,597 A | * 10/1987 | Sanz et al. | 600/512 |
| 5,803,084 A | 9/1998 | Olson | |
| 6,438,410 B2 | * 8/2002 | Hsu et al. | 600/516 |
| 2002/0193696 A1 | * 12/2002 | Hsu et al. | 600/512 |

OTHER PUBLICATIONS

Frank, E.: an accurate, clinically practical system for spatial vectorcardiography, Circulation 13:737, 1956.
Von Der Groeben, J., D.D. Fisher, and J.G. Toole. Temporaspatial Frequency Distribution of P, QRS, and T in Normal Man and Woman.: American Heart Journal, 75 (1968), 487.
Von Der Groeben, J. "Decision Rules in Electrocardiography and Vectorcardiography." Circulation, 36 (1967), 136.

* cited by examiner

Primary Examiner—George Manuel
(74) Attorney, Agent, or Firm—Knechtel, Demeur & Samlan

(57) ABSTRACT

A method of analyzing the electrocardiogram ("ECG") using a set of vectors mathematically derived from the heart vector. The entire ECG waveform of one representative heartbeat is analyzed as a time series of vectors taken at selected time intervals. The vector set consists of the heart vector, the vector of deviation, vector of abnormality, delta vector, the delta vector deviation, and the delta vector abnormality. The analysis system can be applied to two or any greater number of ECG leads represented on planar axes, orthogonal spatial axes, or four or more axes in multidimensional space. The normal range of the ECG in this method is delineated by an adaptive multi-dimensional polyhedron in space to which the unknown ECG is compared. This is accomplished by utilizing a computer platform and the software program to support the required mathematical calculations.

14 Claims, 6 Drawing Sheets

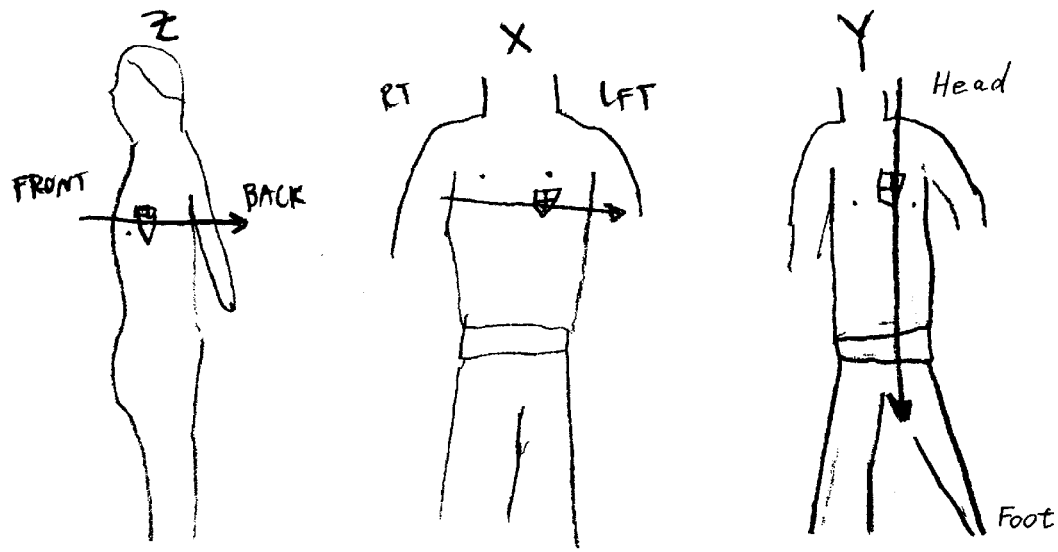
FIG. 3
FIG. 4
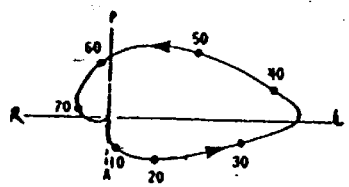
FIG. 5
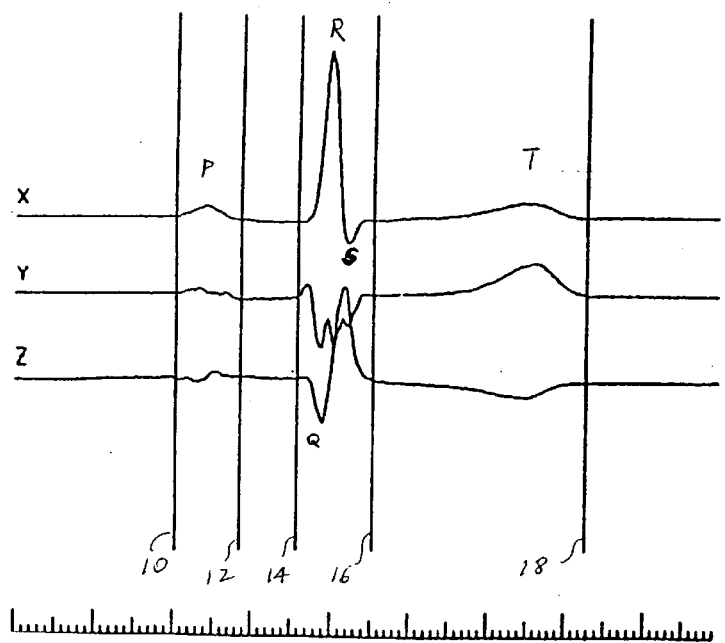

SCALE 1 UNIT = 0.1 millivolt.

METHOD OF ANALYSIS OF THE ELECTROCARDIOGRAM

PRIOR APPLICATION

This application is based upon and claims the priority of Provisional Patent Application number 60/253,575 filed Nov. 28, 2000.

BACKGROUND AND SUMMARY OF THE INVENTION

The electrocardiogram (ECG) presently is analyzed by several different methods. The measurement of the scalar representation of single leads is most common as seen in FIG. 1. The duration and voltage amplitudes of designated deflections, Q, R, S, etc., are measured. Combinations of abnormalities, which are measurements that exceed normal ranges found in selected leads, indicate an abnormality of the myocardium. For example, Q waves of 0.04" duration in leads II, III, and AVF is interpreted as inferior myocardial infarction.

Most commonly the standard 12-lead ECG is analyzed in this way. This system of leads consists of 6 limb leads and 6 leads recorded from the precordial area of the chest as positioned in FIG. 2. These leads measure a voltage difference between a positive and a negative electrode or combinations of electrodes. A positive deflection is recorded when an electrical impulse is coming towards the lead and a negative deflection with the impulse going away from the lead. When looking at the combination of the voltage and duration deflections recorded on the ECG paper, they will provide a predictable pattern which may be analyzed for abnormality. To analyze the pattern, however, it is necessary to further divide the pattern into three different wave complexes: P, QRS, and T complexes (see FIG. 1). The P represents the depolarization of the atrium, QRS the depolarization of the ventricles, and T the repolarization of the ventricles. Different heights, width, and time intervals of the segments may be signs of a pathological condition.

Another method of ECG analysis utilizes three leads, X, Y, and Z, oriented respectively with the right/left, head/foot, and front/back axes of the body as seen in FIG. 3. With this system, two leads are analyzed together in anatomic planes of the torso, the X, Z in the horizontal plane, the X, Y in the frontal plan, and the Y, Z in the sagittal plane. The lead voltages are displayed as time interrupted loops as shown in FIG. 4, which is a horizontal plane display of a normal vectorcardiogram. The loops are analyzed by measuring certain dimensions found useful in diagnosing abnormalities of the myocardium.

In order to analyze each specific time point, it is first necessary to measure the total electrical activity of the heart emitted for a specific point in time. The algebraic sum of this measured electrical activity for that given moment in time will be called the Heart Vector, HV.

By deriving a median HV by finding the medians of the X, Y, and Z measurements from a sample of healthy volunteers, it is possible to compare an individual's HV to this "normalized" HV. There will be defined borders that a normal HV will fall into and any HV that exceeds these borders will be a sign of abnormality. The deviation from median HV will be called the Vector of Deviation, VD. Alternatively, instead of using a grouping or sample of healthy volunteers, a grouping of persons having a specific condition or heart disease can be selected. In this case the individual's HV is compared to the heart vectors of the grouping of persons having the specific condition.

The Vector of Abnormality, VA, is closely related to the Vector of Deviation. They both have the same direction and orientation but have different points of origin. For example, any vector beyond the $95^{th}$ percentile may be defined as the VA. To make the VA as sensitive as possible, it is necessary to transfer the point of origin from (0,0) to the head of the median Heart Vector. The percentile limit surrounding the head of the median HV defines the outermost boundary of normality. We can precisely define the point of origin of VA at this boundary, called point $O_a$. The axes are rotated to achieve this sensitivity. The measured Vector of Abnormality will provide the first criteria used to classify an abnormal condition.

The second criteria used to classify an abnormal condition will be the Delta Vector, or V. The Delta Vector describes the relationship between two HV with respect to time. There is a "normalized" Delta Vector as there is a "normalized" HV, as described above. If the V is measured to be beyond a defined boundary, such as $95^{th}$ percentile, it will indicate abnormality.

By looking at an abnormal vector, VA, as well as the HV's with respect to time, the Delta Vector, it will be possible to characterize the type and severity of the cardiac abnormality. The device used to analyze this will consist of computer hardware for ECG computations and archives, software programs to analyze parameters, and the ability to store records of normal and abnormal populations employed in forming the group envelopes.

The method used in this patent is a mathematical approach and does not depend on a specified display of the ECG from which measurements are taken. It involves the simultaneous analysis of two to any number of leads.

OBJECTS OF THE INVENTION

It is the object of the invention to provide a method of analysis of the orthogonal three lead ECG to determine the presence of abnormality.

It is a further object to provide a device to analyze the orthogonal three lead ECG to determine the presence of abnormality.

Another object is to provide a method of analysis of the orthogonal three lead ECG to distinguish one abnormal condition from all others. A related object is to provide a device to analyze the orthogonal three lead ECG to distinguish one abnormal condition from all others.

Yet another object is to provide a method of analysis of multiple leads (two to any greater number) to determine the presence of abnormality and to distinguish one abnormal condition from all others. A related object is to provide a device to analyze multiple leads (two or more) to determine the presence of abnormality and to distinguish one abnormal condition from all others.

Still another object is to provide a method of analysis of the standard 12-lead ECG to determine the presence of abnormality and to distinguish one abnormal condition from all others.

Yet another object is to provide a method of analysis of regional leads (two or more lead vectors perpendicular to the wave propagation in a region of myocardium) to determine the presence of abnormality and to distinguish one abnormal condition from all others.

Another object is to provide a method of analysis of the ECG and a device to determine the presence of one or multiple abnormalities of the heart.

DESCRIPTION OF THE DRAWINGS

FIG. 3 illustrates the three axes of a three dimensional system.

FIG. 4 is a horizontal plane display of the lead voltages of a normal vectorcardiogram.

FIG. 5 shows the P, QRS, and ST-T complexes of the X, Y, and Z leads.

DESCRIPTION OF THE PREFERRED EMBODIMENT OF THE INVENTION

This invention embodies a method of analysis of the ECG and a device to perform this analysis. The device may be a general purpose computer with adequate memory, or a computer system of specific design to perform only the method of analysis and to display the results. It requires a digitized recording of two or more ECG leads from the body. Analysis is made at selected time increments, which can be from one millisecond (msec) to 20 msec.

The example to be described will use the Frank 3 lead orthogonal system simultaneously recorded and digitized at one millisecond intervals. The recording device may be purchased from any number of manufacturers of ECG Recorder systems, which meet the recording specifications. One example is manufactured by Hewlett Packard, Inc. and is sold under the name PageWriter XLi ECG Recorder. The record to be analyzed is shown in FIG. 5, which illustrates the P, QRS, and ST-T complexes of the X, Y, and Z leads. Vertical cursor lines 10, 12, 14 16 and 18 indicate onsets and offsets.

The onsets and offsets of the P, QRS, and ST-T positions of the ECG will have been selected, and the heart vector (HV) is calculated for each portion of the waveform. The P, QRS, and ST-T are analyzed separately.

Method of Analysis

The unique and innovative part of this invention is the method of analysis of the ECG waveform. This analysis consists of deriving a set of vector quantities related to the heart vector (HV) and is designated as the Digital Heart Vector ("DHV").

Figure 1:
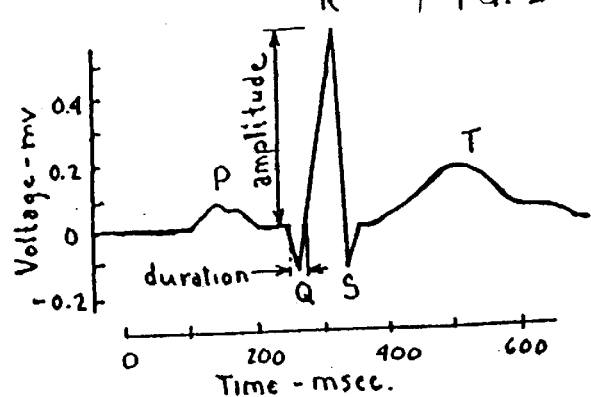
FIG. 1 illustrates the measurement of a scalar electrocardiogram lead.
Figure 2:
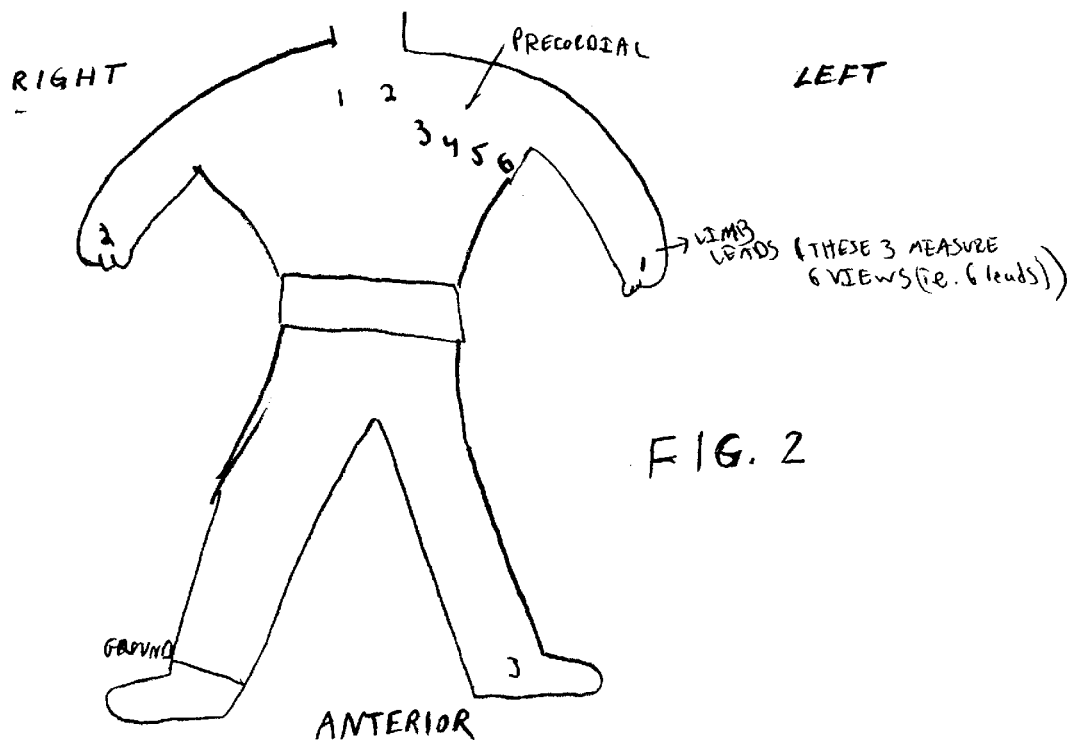
FIG. 2 shows the position of the leads on a patient of a twelve lead display.
Figure 6:
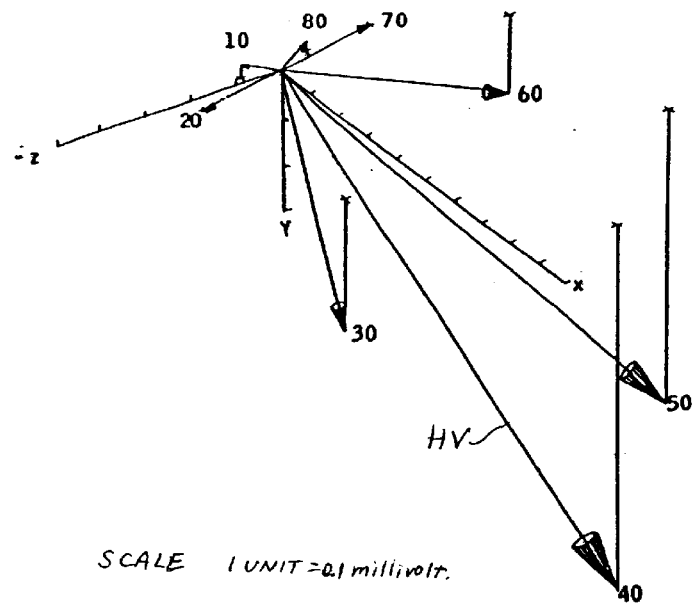
FIG. 6 is a graphic display of the 10 msec time series of heart vectors from the QRS portion of the waveform.

The HV is the equivalent dipole to the summation of all electrical activity at an instant in time produced by the current generator, the myocardium. The time course of the heart's electrical activity generates a series of spatial HV. FIG. 6 shows a representation of the heart vectors for the QRS portion of the waveform at 10 msec time increments from 10 through 80 msec for an individual female, 35 years old.

Use of Polar Coordinates

Figure 7:
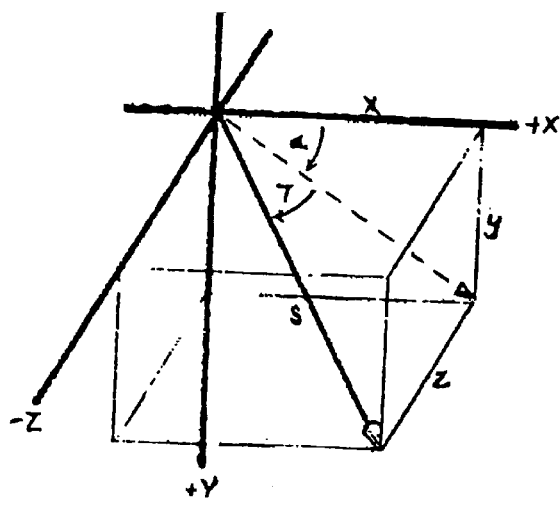
FIG. 7 shows the relationship of a set of polar coordinates and rectangular coordinates.

Both rectangular and polar coordinate systems are used in this methodology. The input data is expressed in rectangular coordinates. However, during rotation of axes, polar coordinates are used. Conversion to and from the coordinate systems occurs throughout the analysis. The set of polar angles chosen is shown in FIG. 7. Alpha ($\alpha$) and tilt (T) angles and length (s) define the vector in three dimensional space. As seen in FIG. 7, the relationship of polar ($\alpha$, T, s) and rectangular (x, y, z) coordinates are:

$$\operatorname{Tan} \alpha = y/x;\ \tan T = z/(x^2+y^2)^{1/2};\ S = (x^2+y^2+z^2)^{1/2}$$

Vector of Deviation

The first in the set of derived vectors is a Vector of Deviation, D. This is defined as follows:

$$D_t = H_t - M_t = (X_h - X_g, Y_h - Y_g, Z_h - Z_g)$$

Where,

D=vector of deviation

H=individual heart vector

M=group median t=instant in time g=point vector-head of M h=point vector-head of H Throughout this application, the term group median heart vector will be used for simplicity. However the inventive process is meant to also include other measures of central tendency such as group mean heart vector and group mode heart vector. Thus "group median heart vector" is defined to include all alternative measures of central tendency.

Figure 11:
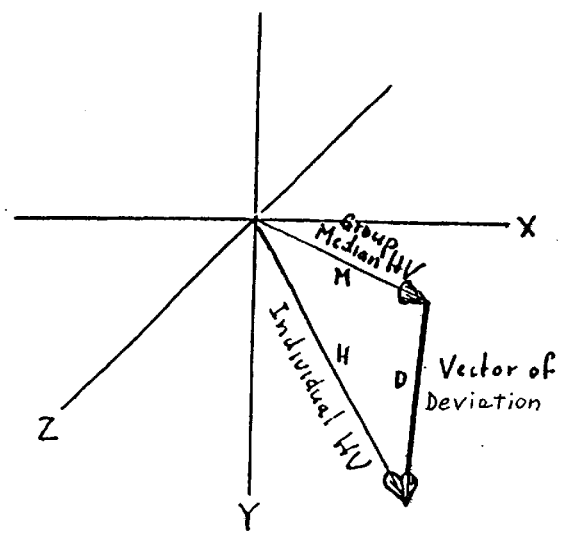
FIG. 11 illustrates the vector of deviation at an instant in time on the X, Y, and Z spatial lead axes.

FIG. 11 shows the vector of deviation, D, at one instant in time for the X, Y, and Z spatial lead axes in which the individual heart vector, H, represents the heart vector. The group median heart vector, M, is derived from a sample of healthy volunteers of the individual's own age and gender. Alternatively, instead of using a grouping or sample of healthy volunteers, a grouping of persons having a specific condition or heart disease can be selected. In such a case the individual's HV is compared to the heart vectors of the grouping of persons having the specific condition. For purposes of discussion, we will use a sample grouping of healthy volunteers.

The individual heart vector, H, is calculated from the averaged X, Y, and Z lead voltages from the person's recording. Vector D represents the deviation of any individual from the group median. It should be noted that there are multiple groups of group median heart vectors as each group of median heart vectors is based on varying parameters such as the age, gender, race, body habitus, etc. for a specific group of individuals.

Representation of Normal and Abnormal Populations

Figure 12:
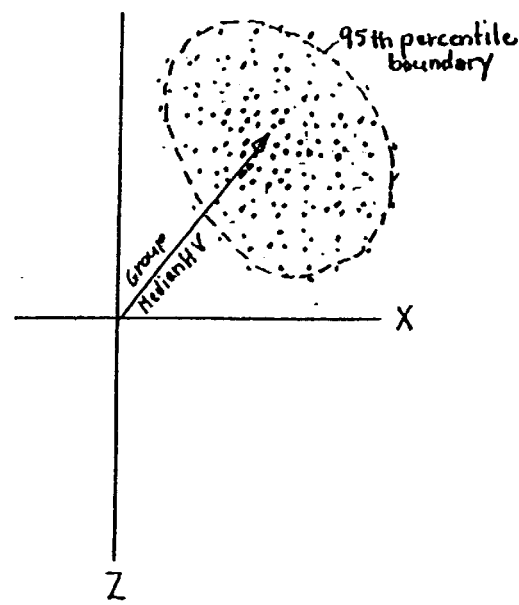
FIG. 12 shows a cluster of heart vector heads of a normal population in two dimensions.

The ECG waveform is recorded from samples of normal and abnormal populations participating in clinical trails. The HV is calculated for each individual. The dispersion of the sample will be represented by the cluster of vector head points plotted in 3 dimensional space for each instant in time as is shown in 2 dimensions in FIG. 12. The cluster of heart vector heads of a normal population in space is illustrated in two dimensions. Group median HV represents the central tendency. The dotted line shows a boundary of a measure of dispersion, which in this case is the boundary of the $95^{th}$ percentile of normals. The group median HV is determined by the median values of the X, Y, Z coordinates. Boundaries are then constructed enclosing selected percentiles of the observations as shown by the dotted line in FIG. 12. A normal population and populations with specific cardiac abnormalities are represented by the vector head clusters in three dimensional space.

The group median heart vector is, $$M=(X_m, Y_m, Z_m)$$

where M=median of $X_1, X_2 \ldots X_n$; $Y_1, Y_2, \ldots Y_n$, $Z_1, Z_2, \ldots Z_n$ and n=number of individual heart vectors in the normal population reference group. Again, it should be noted that the mean or mode may be used instead of the median.

Previous work has been performed in defining appropriate envelopes to delineate limits of normal distribution of the HV, which is known in the prior art. The limits of normal may be defined by envelopes containing a selected measure of dispersion or percentile of normal, e.g. $95^{th}$ or $99^{th}$ percentile. One useful envelope is the three-dimensional polyhedral surface shown in two dimensions as the polygon for ease of illustration in FIG. 13. This perimeter was accomplished by rotating the axis in each plane by 30° and 60° and setting the 2.5 and 97.5 percentile boundaries about the normal group cluster on each axis.

Figure 13:
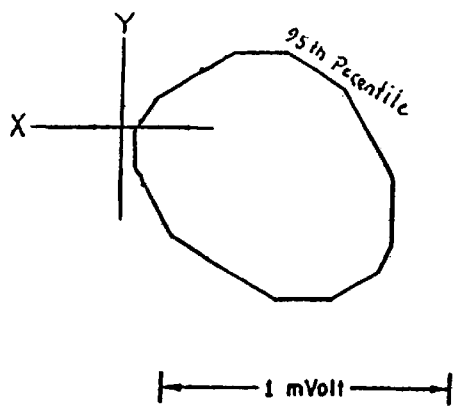
FIG. 13 illustrates a spatial polyhedron envelope of the sagittal plane representation of QRS for males age 35–44 at 70 msec.

In FIG. 13 spatial polyhedral envelopes have been constructed about the distribution of normal subgroups by age and gender. Illustrated is the sagittal plane representation of QRS for males 35–44 at 70 msec shown as a polygon.

Although the specification describes the boundary as being a percentile boundary, is should be understood that this is also meant to encompass other measures of dispersion. The term measure of dispersion is meant to include percentile, standard deviation or standard error or other dispersion measurements.

Vector of Abnormality

Figure 14:
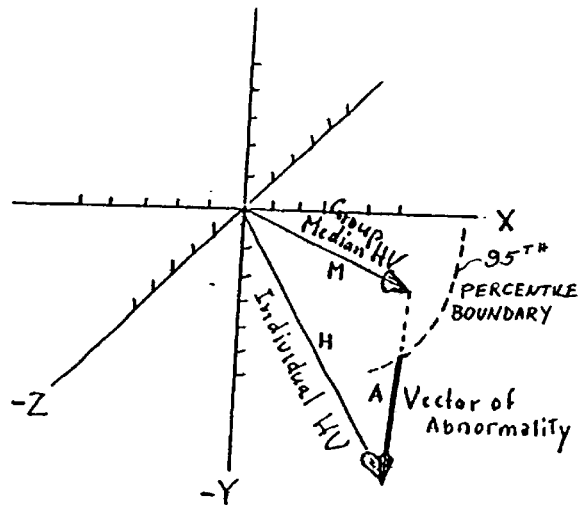
FIG. 14 shows the vector of abnormality originating from the boundary of normal distribution.

The second of the vector set is the Vector of Abnormality A. This vector has the same orientation and sense as the D but its origin is at a selected percentile boundary (e.g. $95^{th}$ percentile) of the vector head cluster of the normal group. Vector A is illustrated in FIG. 14. A is calculated over the entire time series of the P wave, QRS, and ST waves for points in time that the A is positive (i.e. extends beyond the normal boundary). A is considered absent at instants when the A is negative, i.e. within the normal boundary. Vector A of an individual will fall in one or more regions of abnormality. This will be one of the criteria used in classification of an abnormal condition.

In FIG. 14 the Vector of Abnormality A originates from the boundary of normal distribution and has the same direction as the Vector of Deviation. The individual heart vector is shown as H, and the group median heart vector is shown as M The periods in which A vectors are generated constitute the first measure of ECG waveform abnormality. The periods, orientations and magnitudes of A are the first characterization of the type and severity of cardiac abnormality.

Figure 15:
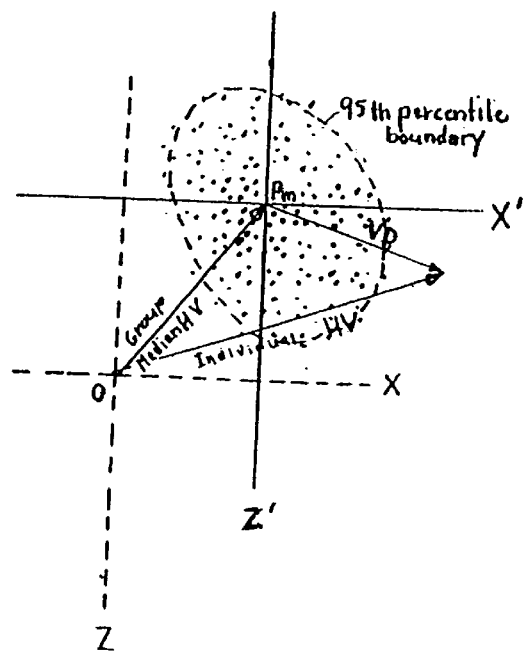
FIG. 15 illustrates the translation of axes from the point of origin to the vector head of the group median heart vector.

Critical to maximizing the sensitivity of this ECG analysis is identifying the point of origin of the vector of abnormality A precisely at the boundary of the envelope surrounding the normal population. This is accomplished as follows:

First, as illustrated in FIG. 15, the axes are translated from O to $P_m$, the vector-head of the group median vector, M:

Translation of axes from origin O to $P_m$:

$$P_m=(X_m-X_O, Y_m-Y_O, Z_m-Z_O) \text{ where } M=(X_m, Y_m, Z_m) \text{ and } P_O=(X_O, Y_O, Z_O)$$

Figure 16:
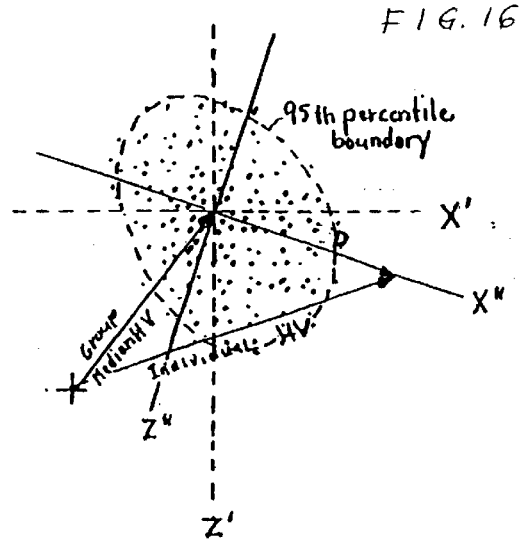
FIG. 16 illustrates the rotation of the coordinate axes to coincide with the vector of deviation.

Next as illustrated in FIG. 16, the axes are rotated so the x-axis coincides with the vector of deviation, D.

That is, axis X is rotated by angles $\alpha$ and T so that D=(s,0,0). From the direction angles of the rotation, the new coordinates of any point are:

$$X''=X'\cos \alpha$$

$$Y''=Y'\cos \beta$$

$$Z''=Z'\cos \gamma$$

Finding the $O_A$ of A, vector of abnormality with an iterative calculation, rotate $X_r$ by an angle $\theta$ so that:

$$X_r 2.5/97.5\%=\text{Minimum } O_A$$

$$\text{Then } O_A=X''/\cos \theta$$

$$\text{And } A=D-O_A$$

Figure 17:
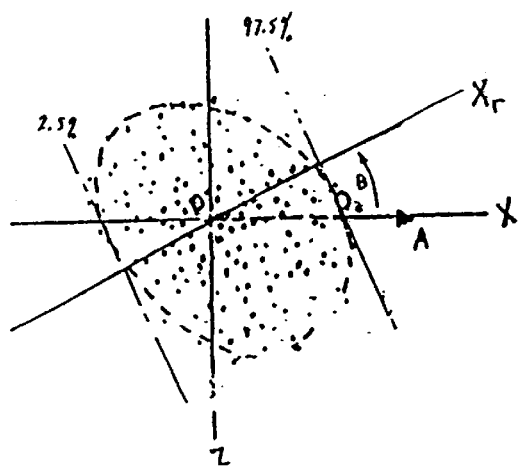
FIG. 17 illustrates the rotation of the X axis to find the origin of the vector of abnormality at the 2.5% and 97.5% distribution limits.

FIG. 17 illustrates the rotation of axis $X_r$ to find the origin of A at the 2.5/97.5% distribution limits and to define the extent the vector of abnormality exceeds normal limits.

Delta Vector

The final vector in the analysis is a Delta Vector, V, which is defined as follows:

$$V_{t2}=H_{t2}-H_{t1}$$

where V=Delta Vector

H=individual HV t=instant in time

Figure 18:
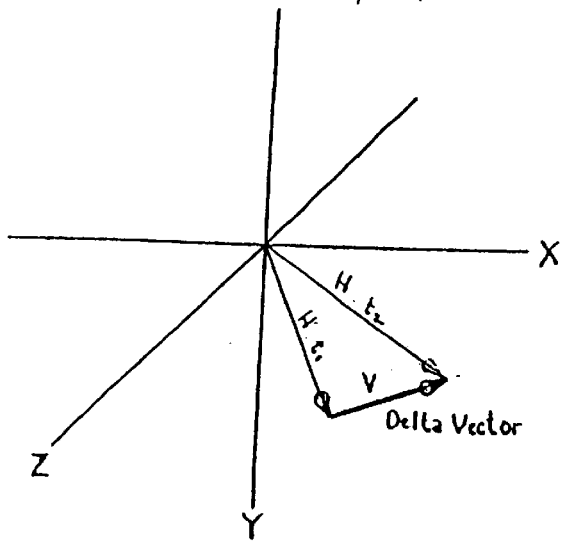
FIG. 18 shows the delta vector on a three spatial lead axes.

FIG. 18 illustrates the Delta Vector V between time 1 and time 2 in which X, Y, and Z are the spatial lead axes and H equals the heart vector.

Figure 19:
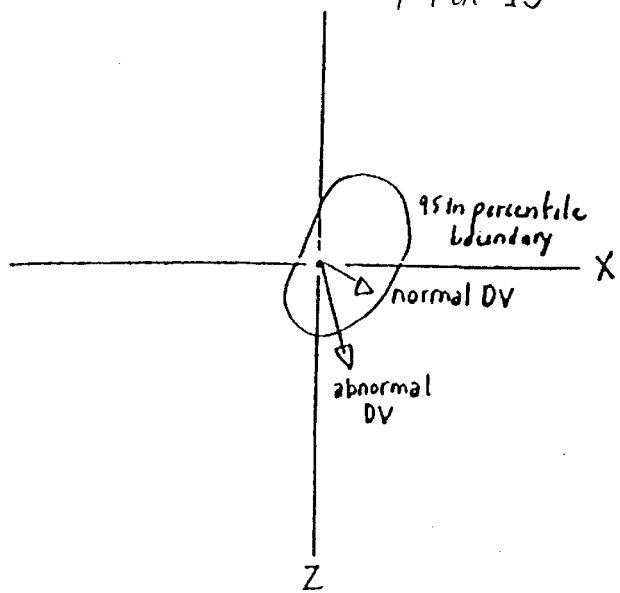
FIG. 19 shows examples of differing trajectories of the delta vector and normal and abnormal delta vectors delineated by the $95^{th}$ percentile.

Just as there is a normal group vector-head cluster of the HV describing normal distribution, there is a normal group distribution for the V between two instants in time. There is a delta vector of deviation based on the individual person's Delta Vector, V, and a group median delta vector. Vector V is further analyzed as to whether it falls inside or outside a normal distribution boundary (e.g., the $95^{th}$ percentile.) There will be a "normalized" Delta Vector as there is a "normalized" HV, as described above. This is shown in FIG. 19 in two dimensions although 3 dimensions (X, Y, and Z) are actually used in this calculation. FIG. 19 illustrates an example of differing trajectories of the Delta Vector V and normal or abnormal V delineated by the $95^{th}$ percentile.

The periods of the generated vector A in combination with the vector V just prior to, and just after the period of the A further characterize the type and severity of the cardiac abnormality by distinguishing one abnormal state from another.

Example Calculation

The following input data is given: Patient name, patient number, patient age (which in the example is a 48 year old male) and the patient history (which in this case includes hypertension). In the analysis of the QRS portion of his DHV, the 40 msec. time point of his heart (H in mvolts) is (+1.83, +0.37, +0.81). From the stored data on normals, the group median vector for males 45 to 54 years of age is (+1.07, +0.65, +0.11).

Figure 8:
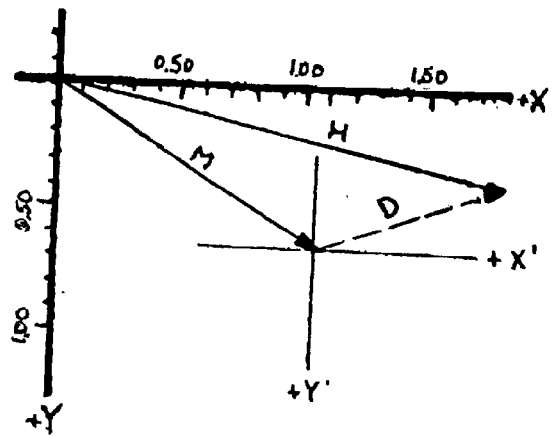
FIG. 8 shows the relationship of a patient's heart vector, group median heart vector and vector of deviation in a frontal plane projection.

To derive the vector of deviation, D, subtract M from H. The patient's D is (+0.76, −0.28, +0.70). The relation of H, M, and D is shown in FIG. 8 in the frontal plane projection. Translate D to axes X', Y', Z', whose origin is the spatial median center of normal distribution. The coordinates are the same by the Law of Parallelograms.

Figure 9:
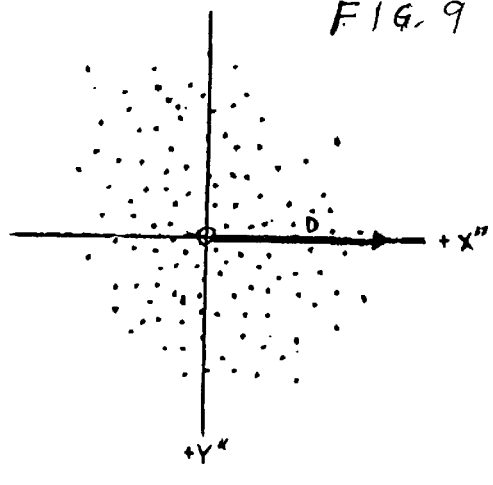
FIG. 9 illustrates the position of the vector of deviation within a spatial cluster of normal vectors in a frontal plane projection after translation and rotation of axes X", Y" and Z".

In the next step, rotate the axes so that the X' axis coincides with D. The coordinates of vector head D become (s, 0, 0, or +1.07, 0, 0) by definition. The position of D within the spatial cluster of normal vectors is shown in the frontal plane projection in FIG. 9.

A vector of abnormality, A, has the same direction as D so only its magnitude need be determined. The origin ($O_A$) of A must be identified as the minimum possible value of the 97.5 percentile of normal distribution.

To find $O_A$, perform an iterative calculation by rotating the $X_r$ by the angle of θ throughout the hemisphere which have values greater than 0. In this process all points in space projected onto the $X_r$ will be the x coordinate values. The y and z values are not used in the determination. The $X_r$ values of x become a scalar distribution to determine the 2.5 and 97.5 percentile limits whichever is needed.

Figure 10:
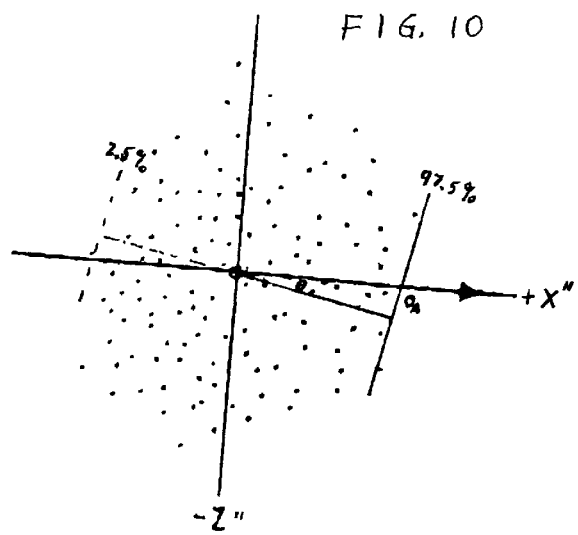
FIG. 10 illustrates the solution of the iterative calculation in the horizontal plane.

Using iterative calculations, the minimum of OA is found by rotating $X_r$ through angle θ at increments of 1 degree. In this case, OA is minimum at 10 degrees and the 97.5% point is 0.68. At this point $O_A$=0.69. Therefore $A=D-O_A$ or 1.07−0.69=0.38 mvolts. The direction of A is the same as D. FIG. 10 illustrates the solution of the iterative calculation as seen in the horizontal plane.

Following the same procedures used to determine A, the abnormalities of the delta vectors ($A_y$) preceding and following H are determined ($V_{t-1}, V_{t+1}$). The severity and type of cardiac abnormality manifested in the DHV are characterized by the periods of the presence of A and their associated normal or abnormal delta vectors. The abnormalities in this patient indicate the presence of left ventricular hypertrophy.

Device to Perform the Method of Analysis

The device will consist of computer hardware capable of providing the platform for the computations and archiving of ECG records, software programs to compute the analysis parameters and store records of normal and abnormal populations employed in forming the group envelopes. The device may be a general purpose computer with adequate memory, or a computer system of specific design to process the ECG, to perform the method of analysis and to display the results.

While the invention has been described in conjunction with a specific embodiment, it is evident that many alternatives, modifications and variations will be apparent to those skilled in the art in light of the foregoing description. Accordingly, it is intended to embrace all such alternatives, modifications and variations as fall within the spirit and scope of the appended claims.

What is claimed is:

1. A method for analyzing an electrocardiograph heart signal comprising the steps of:
   (a) establishing a group median heart vector for a selected time increment based upon individual heart vectors of a sample of a specified grouping of persons, the group median heart vector having a digitized value;
   (b) establishing a distribution of individual heart vectors for the selected time increment of the specified grouping of persons upon which a means of dispersion boundary is derived;
   (c) producing a digitized signal of at least two leads from an electrocardiograph of a patient corresponding to the selected time increment;
   (d) deriving a patient heart vector for the digitized signal;
   (e) deriving a vector of deviation corresponding to the selected time increment based on the derived patient heart vector and the group median heart vector; and
   (f) deriving a vector of abnormality for the selected time increment having a point of origin at the selected percentile boundary of the distribution of individual heart vectors.

2. The method of claim 1 and the added steps of establishing a group median heart vector for additional selected time increments and producing additional digitized signals of the at least two leads at other selected time increments.

3. The method of claim 2 and the added steps of deriving additional patient heart vectors and vectors of deviation for each of the digitized signals, and deriving vectors of abnormality for each of the additional time segments.

4. The method of claim 3 and the further step of defining a percentile envelope of the digitized value of the distribution of individual heart vectors of the sample of specified grouping of persons.

5. The method of claim 4 and the added step of characterizing the type and severity of cardiac abnormality based upon the selected time segment, orientation and magnitude of the vectors of abnormality.

6. The method of claim 4 and the further step of selecting the measure of dispersion boundary of the envelope of the distribution of individual heart vectors of the sample of the specified grouping of persons between the $95^{th}$ and $99^{th}$ percentile.

7. The method of claim 1 wherein the selected time increment is selected from the P, PQ, QRS, or ST-T segments of the electrocardiograph.

8. The method of claim 1 wherein the group median heart vector is calculated from any group of individual heart vectors in multi-dimensional space.

9. The method of claim 1 wherein the vector of deviation is calculated as the difference between the value of the heart vector and the value of the group median heart vector.

10. The method of claim 1 wherein the point of origin of the vector of abnormality is found by determining the selected percentile on an axis which is rotated until the origin of the vector of abnormality is at a minimum value.

11. The method of claim 1 and the further step of establishing a establishing individual delta vectors of the sample of the specified grouping of persons and establishing a group median delta vector between two selected time increments based upon the individual delta vectors and deriving a patient delta vector between two patient heart vectors at the two selected time increments and a delta vector of deviation based on the patient delta vector and the group median delta vector.

12. The method of claim 11 and the further step of establishing a distribution of delta vectors of the sample of the specified grouping of persons.

13. The method of claim 12 and the further step of deriving a delta vector of abnormality having a point of origin at a selected measure of dispersion boundary of the distribution of delta vectors of the sample of the specified grouping of persons.

14. The method of claim 13 and the further step of characterizing the type and severity of cardiac abnormality based upon combinations of vectors of abnormality and delta vectors.

* * * * *